US00PP37481P2

(12) United States Plant Patent
Mathey

(10) Patent No.: US PP37,481 P2
(45) Date of Patent: Jun. 23, 2026

(54) ***PHYSOCARPUS* PLANT NAMED 'SMNPOE'**

(50) Latin Name: *Physocarpus opulifolius*
Varietal Denomination: SMNPOE

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,650

(22) Filed: Nov. 8, 2025

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP36,138 P2 * 9/2024 Wood ..... A01H 6/74
Plt./226

* cited by examiner

*Primary Examiner* — Karen M Redden
(74) *Attorney, Agent, or Firm* — C. Anne Whealy

(57) ABSTRACT

A new and distinct cultivar of *Physocarpus* plant named 'SMNPOE', characterized by its compact, upright to outwardly spreading and low mounding plant habit; vigorous growth habit; freely branching habit; dense and bushy appearance; developing leaves that are burnt orange in color with yellow green-colored margins that mature to a bright green color with development; numerous dense corymbs with white-colored flowers; resistance to Powdery Mildew; and good garden performance.

3 Drawing Sheets

Figure 1:
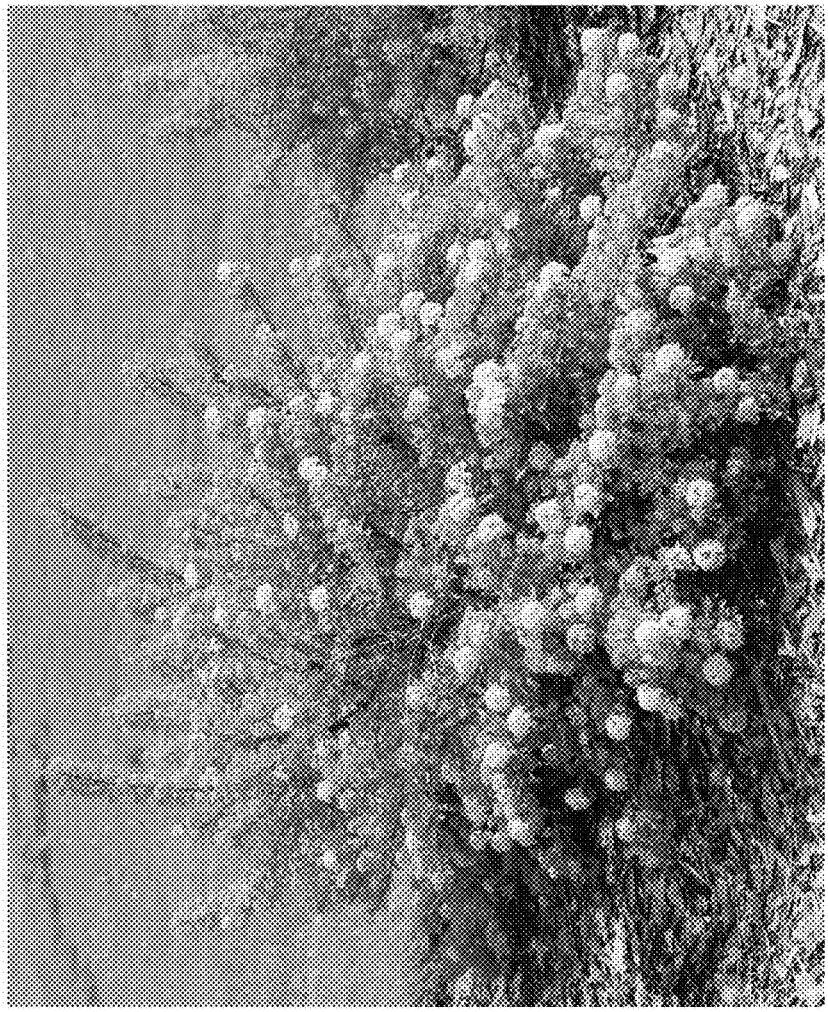

Botanical designation: *Physocarpus opulifolius*.
Cultivar denomination: 'SMNPOE'.

BACKGROUND OF THE INVENTION

The present invention relates to a new and distinct cultivar of *Physocarpus* plant, botanically known as *Physocarpus opulifolius*, commonly referred to as Ninebark and hereinafter referred to by the cultivar name 'SMNPOE'.

The new *Physocarpus* is a product of a planned breeding program conducted by the Inventor in Grand Haven, Michigan. The objective of the breeding program was to develop new compact and freely branching *Physocarpus* plants with unique leaf shape and color.

The new *Physocarpus* plant originated from an open-pollination during the summer of 2017 in Grand Haven, Michigan of a proprietary selection of *Physocarpus opulifolius* referred to as "Tiny Green", not patented, as the female, or seed, parent with an unknown proprietary selection of *Physocarpus opulifolius* as the male, or pollen, parent. The new *Physocarpus* plant was discovered and selected by the Inventor during the summer of 2021 as a single flowering plant within the progeny of the stated cross-pollination in a controlled environment in Grand Haven, Michigan.

Asexual reproduction of the new *Physocarpus* plant by softwood stem cuttings in a controlled greenhouse environment in Grand Haven, Michigan since the summer of 2021 has shown that the unique features of this new *Physocarpus* plant are stable and reproduced true to type in successive generations of asexual reproduction.

SUMMARY OF THE INVENTION

Plants of the new *Physocarpus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNPOE'. These characteristics in combination distinguish 'SMNPOE' as a new and distinct *Physocarpus* plant:

1. Compact, upright to outwardly spreading and low mounding plant habit.
2. Vigorous growth habit.
3. Freely branching habit; dense and bushy appearance.
4. Developing leaves that are burnt orange in color with yellow green-colored margins that mature to a bright green color with development.
5. Numerous dense corymbs with light pink-colored flower buds that develop into white-colored flowers.
6. Resistant to Powdery Mildew.
7. Good garden performance.

Plants of the new *Physocarpus* can be compared to plants of the female parent selection, "Tiny Green". In side-by-side comparisons, plants of the new *Physocarpus* differ primarily from plants of "Tiny Green" in the following characteristics:

1. Mature plants of the new *Physocarpus* are smaller than mature plants of "Tiny Green".
2. Leaves of plants of the new *Physocarpus* are brighter green in color than leaves of plants of "Tiny Green".

Plants of the new *Physocarpus* can be compared to plants of *Physocarpus opulifolius* 'ZLEMichael', disclosed in U.S. Plant Pat. No. 34,243. In side-by-side comparisons, plants of the new *Physocarpus* differ primarily from plants of 'ZLEMichael' in the following characteristics:

1. Plants of the new *Physocarpus* are more spreading and low mounding than and not as upright as plants of 'ZLEMichael'.
2. Mature plants of the new *Physocarpus* are smaller than plants of 'ZLEMichael'.

BRIEF DESCRIPTION OF THE PHOTOGRAPHS

The accompanying colored photographs illustrate the overall appearance of the new *Physocarpus* plant showing the colors as true as it is reasonably possible to obtain in colored reproductions of this type. Colors in the photographs may differ slightly from the color values cited in the detailed botanical description which accurately describe the colors of the new *Physocarpus* plant.

The photograph on the first sheet (FIG. 1) is a side perspective view of a typical flowering plant of 'SMNPOE'.

Figure 2:
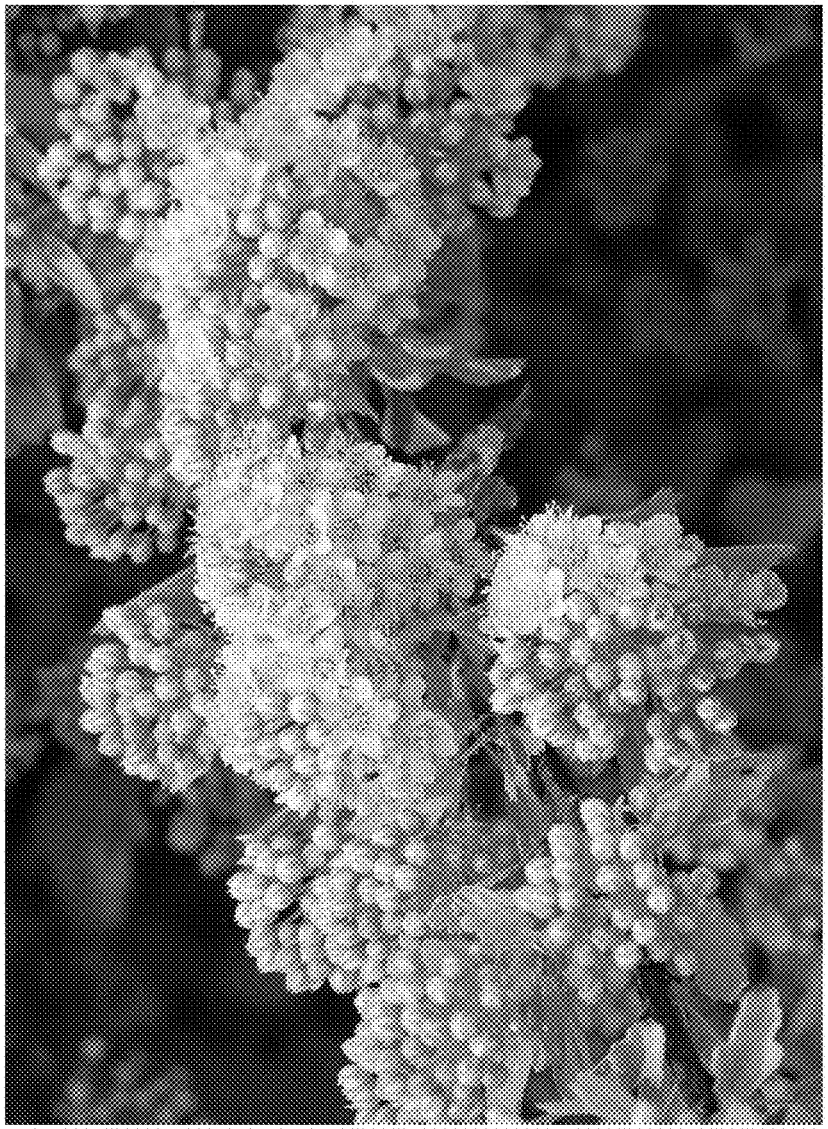

The photograph on the second sheet (FIG. 2) is a close-up view of a typical flowering stem of 'SMNPOE'.

Figure 3:
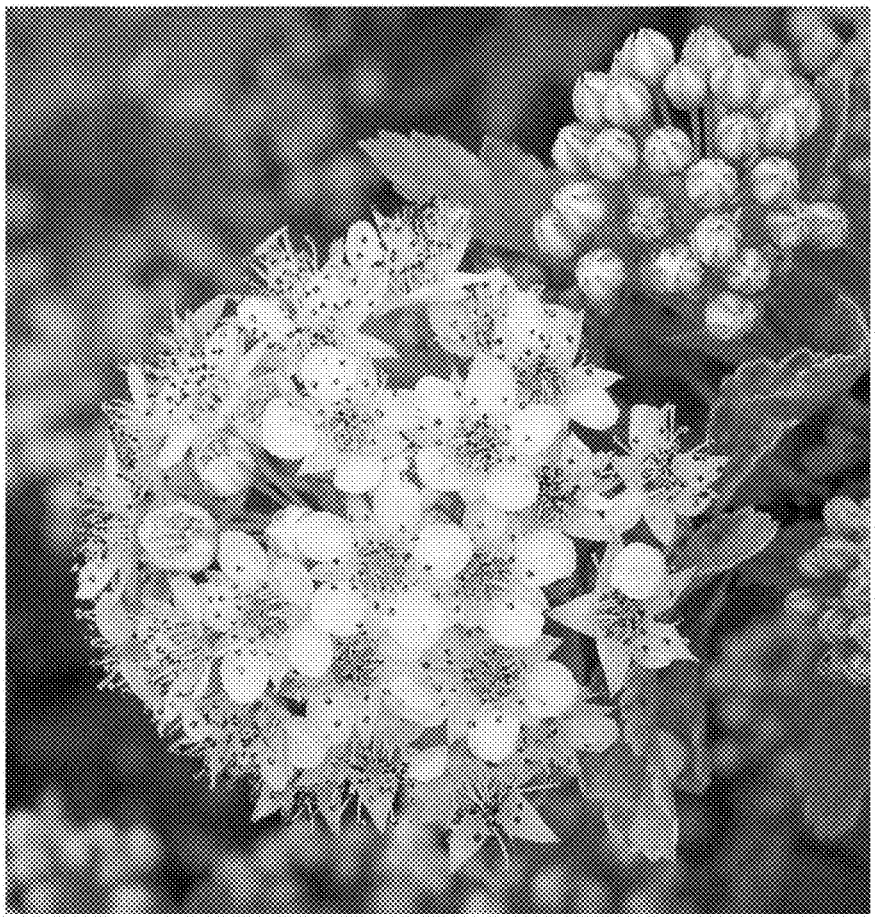

The photograph on the third sheet (FIG. 3) is close-up view of a typical inflorescence of 'SMNPOE'.

Plants used for the aforementioned photographs were grown in an outdoor nursery in Grand Haven, Michigan during late spring and summer and were two years old.

DETAILED BOTANICAL DESCRIPTION

The following observations, measurements and values describe plants grown in the late spring and early summer in three-gallon containers in a polyethylene-covered greenhouse in Grand Haven, Michigan and under cultural practices typical of commercial *Physocarpus* production. During the production of the plants, day temperatures ranged from 18° C. to 27° C. and night temperatures ranged from 5° C. to 10° C. Plants were two years old when the detailed description were taken. In the description, color references are made to The Royal Horticultural Society Colour Chart, 2015 Edition, except where general terms of ordinary dictionary significance are used.

Botanical classification: *Physocarpus opulifolius* 'SMNPOE'.

Parentage:

*Female, or seed, parent*.—Proprietary selection of *Physocarpus opulifolius* referred to as "Tiny Green", not patented.

*Male, or pollen, parent*.—Unknown proprietary selection of *Physocarpus opulifolius*, not patented.

Propagation:

*Type*.—By softwood stem cuttings.

*Time to initiate roots, summer*.—About 25 days at temperatures ranging from about 18° C. to 27° C.

*Time to produce a rooted young plant, summer*.—About 60 days at temperatures ranging from about 18° C. to 27° C.

*Root description*.—Medium in thickness; fleshy to fibrous; typically white and/or brown in color, actual color of the roots is dependent on substrate composition, water quality, fertilizer, substrate temperature and physiological age of roots.

*Rooting habit*.—Freely branching; medium density to dense.

Plant description:

*Plant form and growth habit*.—Perennial deciduous shrub; compact, upright to outwardly spreading and low mounding plant habit; vigorous growth habit and moderate growth rate.

*Plant height, soil level to top of foliar plane*.—About 30 cm.

*Plant height, soil level to top of floral plane*.—About 30 cm.

*Plant diameter* (*area of spread*).—About 50 cm.

Lateral branch description:

*Branching habit*.—Freely branching habit; dense and bushy appearance with about eight primary lateral branches each with about 15 secondary lateral branches developing per plant.

*Length*.—About 25 cm.

*Diameter*.—About 3 mm.

*Internode length*.—About 2.25 cm.

*Aspect*.—Erect to about 20° from vertical.

*Strength*.—Moderately strong to strong.

*Texture and luster*.—Smooth, glabrous; longitudinally ridged; semi-glossy.

*Color, developing*.—Close to 144B.

*Color, developed*.—Close to 144B; if woody, close to 200A to 200B.

Leaf description:

*Arrangement*.—Alternate, simple.

*Length*.—About 5 cm.

*Width*.—About 3.5 cm.

*Shape*.—Ovate.

*Apex*.—Acute.

*Base*.—Obtuse.

*Margin*.—Lobed and doubly serrate; sinuses medium in depth.

*Texture and luster, upper and lower surfaces*.—Smooth, glabrous; semi-glossy.

*Venation pattern*.—Pinnate.

*Color*.—Developing leaves, upper and lower surfaces: Close to N167A; at the margins, close to 144A. Fully expanded leaves, upper surface: Close to 146A; venation, close to 146A; leaves do not change color in the autumn. Fully expanded leaves, lower surface: Close to 146B; venation, close to 146B; leaves do not change color in the autumn.

*Petioles*.—Length: About 2 mm. Diameter: About 1 mm. Texture and luster, upper and lower surfaces: Smooth, glabrous; semi-glossy. Color, upper and lower surfaces: Close 144B.

Flower description:

*Flower appearance and arrangement*.—Star-shaped rotate flowers arranged in terminal and axillary corymbs; freely flowering habit with about 30 flowers per inflorescence and about 4,000 flowers developing per plant; flowers face upright to outwardly depending on their position on the corymb.

*Fragrance*.—None detected.

*Natural flowering season*.—Plants flower during the early summer (May to June) in Michigan.

*Flower longevity*.—Depending on temperature, individual flowers last about two weeks on the plant; flowers not persistent.

*Flower buds*.—Length: About 3 mm. Diameter: About 3 mm. Shape: Globose. Texture and luster: Smooth, glabrous; matte. Color: Close to 155C tinged with close to 63C.

*Inflorescence height*.—About 2.5 cm.

*Inflorescence diameter*.—About 3 cm.

*Flower diameter*.—About 6 mm.

*Flower length* (*depth*).—About 4 mm.

*Petals*.—Quantity and arrangement: Five in a single whorl, not fused. Length: About 3 mm. Width: About 3 mm. Shape: Orbicular. Apex: Obtuse. Base: Obtuse. Margin: Entire; not undulate. Texture and luster, upper and lower surfaces: Smooth, glabrous; silky; matte. Color: When opening and fully opened, upper surface: Close to 155C; venation, close to 155C; color does not change with subsequent development. When opening and fully opened, lower surface: Close to 155C; venation, close to 155C; color does not change with subsequent development.

*Sepals*.—Quantity and arrangement: Five in a single whorl fused at the base into a stellate-shaped calyx. Length: About 3 mm. Width: About 2 mm. Shape: Deltoid. Apex: Narrowly acute. Margin: Entire. Texture and luster, upper and lower surfaces: Smooth, glabrous; matte. Color: When opening and fully opened, upper surface: Close to 145C. When opening and fully opened, lower surface: Close to 144A to 144B.

*Peduncles*.—Length: About 2 cm. Diameter: About 2 mm. Aspect: About 20° to 60° from the lateral branch axis. Strength: Moderately strong. Texture and luster: Smooth, glabrous; semi-glossy. Color, upper and lower surfaces: Close to 144A.

*Pedicels*.—Length: About 1 cm. Diameter: About 1 mm. Aspect: About 45° from the peduncle axis. Strength: Moderately strong. Texture and luster: Smooth, glabrous; semi-glossy. Color, upper and lower surfaces: Close to 144A.

*Reproductive organs*.—Stamens: Quantity per flower: About 35.Filament length: About 3 mm. Filament color: Close to NN155A. Anther length: About 0.5 mm. Anther shape: Globose. Anther color: Close to 65C. Pollen amount: Sparse to moderate. Pollen color: Close to 155A. Pistils: Quantity per flower: About four. Pistil length: About 3 cm. Style length: About 2.5 cm. Style color: Close to 12D. Stigma diameter: About 0.5 mm. Stigma shape: Rounded. Stigma color: Close to 12C. Ovary color: Close to 12D. Fruits and seeds: To date, fruit and seed development has not been observed on plants of the new *Physocarpus*.

Garden performance: Plants of the new *Physocarpus* have been observed to have good garden performance and tolerate rain, wind and to be suitable for USDA Hardiness Zones 3 through 7.

Pathogen & pest resistance: Plants of the new *Physocarpus* have been shown to be resistant to Powdery Mildew (*Podosphaera physocarpi*). To date, plants of the new *Physocarpus* have not been shown to be resistant to pests and other pathogens common to *Physocarpus* plants.

It is claimed:

1. A new and distinct *Physocarpus* plant named 'SMN-POE' as herein illustrated and described.

* * * * *